(12) United States Patent
Messing et al.

(10) Patent No.: US 6,733,497 B2
(45) Date of Patent: *May 11, 2004

(54) CLAMSHELL DISTAL CATHETER ASSEMBLY

(75) Inventors: Katie Messing, San Jose, CA (US); Jon Wohlgemuth, Morgan Hill, CA (US); Robert Bencini, Sunnyvale, CA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/903,402

(22) Filed: Jul. 9, 2001

(65) Prior Publication Data

US 2003/0009163 A1 Jan. 9, 2003

(51) Int. Cl.[7] .............................................. A61B 18/14
(52) U.S. Cl. ........................................ 606/41; 600/920
(58) Field of Search ....................... 606/27–33, 41–50; 607/100–102

(56) References Cited

U.S. PATENT DOCUMENTS

| | | | | |
|---|---|---|---|---|
| 5,370,678 A | * | 12/1994 | Edwards et al. ............ | 607/101 |
| 5,685,878 A | * | 11/1997 | Falwell et al. ................ | 606/41 |
| 5,782,900 A | * | 7/1998 | de la Rama et al. .......... | 606/41 |
| 5,916,158 A | * | 6/1999 | Webster, Jr. ................. | 606/41 |
| 5,964,757 A | * | 10/1999 | Ponzi ........................... | 606/45 |
| 6,078,830 A | * | 6/2000 | Levin et al. ................... | 606/41 |
| 6,176,857 B1 | * | 1/2001 | Ashley ......................... | 606/41 |
| 6,312,425 B1 | * | 11/2001 | Simpson et al. .............. | 606/41 |
| 6,405,067 B1 | * | 6/2002 | Mest et al. .................... | 606/41 |

* cited by examiner

*Primary Examiner*—Roy D. Gibson
*Assistant Examiner*—Henry M. Johnson
(74) *Attorney, Agent, or Firm*—Bingham McCutchen LLP

(57) ABSTRACT

Distal catheter assemblies, catheters, and methods for minimizing damage to heat and/or magnetically sensitive components are provided. A distal catheter assembly comprises a composite housing having a cavity formed therein and first and second complementary lateral housing sections. A first component, e.g., a sensor, is mounted within the first housing section. Optionally, a second component, e.g., a steering assembly or RF wire, can also be mounted to the first housing section. The open housing section allows the first and second components to be mounted in any order. Thus, if the first component is mounted last, any adverse effects on the first component that may otherwise result from mounting the components in the reverse order may be minimized. After the first and second components are mounted, the first and second housing sections are affixed to each other in a suitable manner, e.g., by using a pin and hole arrangement. In the preferred embodiment, the composite housing includes a cap-shaped head and a cylindrical neck section, with the head forming an ablation electrode. In this case, the head can further include a channel for mounting a thermistor therein. Either or both the head and neck can be formed from the first and second housing sections. The distal catheter assembly can be mounted to the distal end of a catheter tube to form a fully functioning catheter.

23 Claims, 8 Drawing Sheets

CLAMSHELL DISTAL CATHETER ASSEMBLY

RELATED APPLICATIONS

This application is being filed concurrently with application Ser. Nos. 09/903,112, entitled "Distal Catheter Assembly With Proximal Mounting Member," and 09/903,111, entitled "Two-Piece Distal Catheter Assembly," both of which are expressly incorporated herein by reference.

TECHNICAL FIELD

The present invention generally relates to medical devices, and more particularly, to methods of assembling catheter tips with sensors.

BACKGROUND OF THE INVENTION

Catheters are widely used in the medical arts. For example, catheters are sometimes inserted into a patient's body during mapping and ablation procedures of the patient's heart. Catheters used for such procedures typically comprise of electrode tips and electrode rings. Various other components may also be incorporated into these medical catheters. For example, a steering mechanism allowing the physician to control the movement of the catheter while the catheter is in a patient's body may be incorporated into the catheter. A thermistor or a thermocouple may also be placed at the catheter tip to provide temperature data. In addition, such catheters may incorporate other sensors at the tip to assist the physician in performing these delicate procedures.

One type of sensor currently being incorporated into catheter tips is an electromagnetic sensor, which provides important information to the physician about the exact location of the catheter tip relative to the patient's body. An electromagnetic sensor used for such purposes and commercially available is a "3D" sensor, which employs an orthogonal arrangement of three sensor pairs to provide three-dimensional position coordinates of the catheter tip. Details on the structure and use of a "3D" sensor are discussed in PCT publication WO 00/10456, entitled "Intrabody Navigation System for Medical Applications," which is hereby expressly and fully incorporated herein by reference.

Incorporating such sensors into catheter tips during assembly can be difficult. Catheters used in, for example RF ablation and mapping procedures, tend to be very small in size, thus requiring assembly techniques that must be precise. In addition, electromagnetic sensors are highly sensitive to excess thermal energy and magnetic fields. Even short exposure to excess thermal energy and magnetic fields may cause damage to these sensors. Thus, the assembly of distal catheter assemblies that contain electromagnetic sensors are further constrained, since certain heat generating steps, for example soldering, may potentially expose these sensors to excess heat. Further, many of the components incorporated into these devices are made from ferrous material, such as stainless steel, which can magnetically affect the sensors. Thus, a method for assembling a distal catheter assembly without damaging a magnetic and heat-sensitive component contained therein would be highly desirable.

SUMMARY OF THE INVENTION

The present inventions include distal catheter assemblies, catheters, and methods that minimize damage to sensitive components.

In accordance with a first aspect of the present inventions, a distal catheter assembly comprises a composite housing having a cavity formed therein. The composite housing comprises first and second complementary lateral housing sections, i.e., the lateral sides of the housing sections fit together in a complementary fashion. The housing sections are affixed to each other in a suitable manner, e.g., in a pin and hole arrangement. By way of non-limiting example, the housing can include a cap-shaped head and a cylindrical neck. In this case, the head may form an ablation electrode, and ring electrodes, such as mapping electrodes, may be disposed around the neck. A channel may be formed distal to the cavity, where a thermistor can be disposed. Either or both of the head and neck can be formed by the complementary housing sections.

The distal catheter assembly further comprises a component, such as a sensor, mounted within the cavity. The distal catheter assembly may optionally include a second component mounted in the cavity proximal to the first component. The second component can be, e.g., a steering assembly, and if the housing comprises an ablation electrode, an RF lead.

In accordance with a second aspect of the present inventions, a method for assembling a distal catheter assembly comprises mounting a component within a first lateral housing section, and affixing a complementary second lateral housing section to the first housing section subsequent to mounting the component. After mounting the component, the housing sections are affixed to each other in a suitable manner, e.g., in a pin and hole arrangement, to form a composite housing. By way of non-limiting example, the housing can form an ablation electrode, in which case, the housing can include a channel, where a thermistor can be optionally mounted therein.

Optionally, a second component can be mounted within the first housing section by suitable means, e.g., heat generation, and more specifically, soldering. The second component can be, e.g., a steering assembly, and if the housing comprises an ablation electrode, an RF lead. The openness of the first lateral housing section allows the components to be mounted in any order. Preferably, the second housing section is affixed to the first housing section subsequent to mounting the second component. In this manner, the second component can be more easily mounted within a housing. The first component is preferably mounted to the first housing section subsequent to the second component. In this manner, any adverse effects on the first component that would otherwise result from mounting the first component prior to mounting the second component can be minimized or completely eliminated.

DESCRIPTION OF THE PREFERRED EMBODIMENTS

The present inventions provide for novel distal catheter assemblies containing magnetic- and heat-sensitive components, and methods for manufacturing the same. The methods provided are for various distal catheter assembly designs, including unibody, two-member, and clamshell distal catheter assemblies. The different assembly techniques used in the methods provided may include, for example, front- and back-loading assembly techniques. It is noted that, to the extent that the features of the various assemblies and methods described below are similar, they have been similarly illustrated and identical reference numbers have been used.

Figure 1:
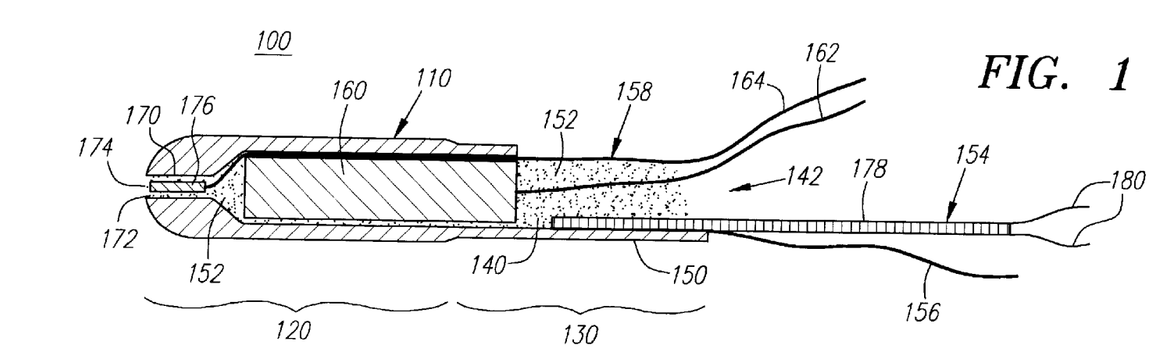
FIG. 1 is a longitudinal-sectional view of an exemplary distal catheter assembly constructed in accordance with the present inventions, wherein the distal catheter assembly is formed of a unibody ablation electrode with a front-loaded sensor, and a steering assembly and RF wire are mounted thereto using heat generating means.
Figure 2:
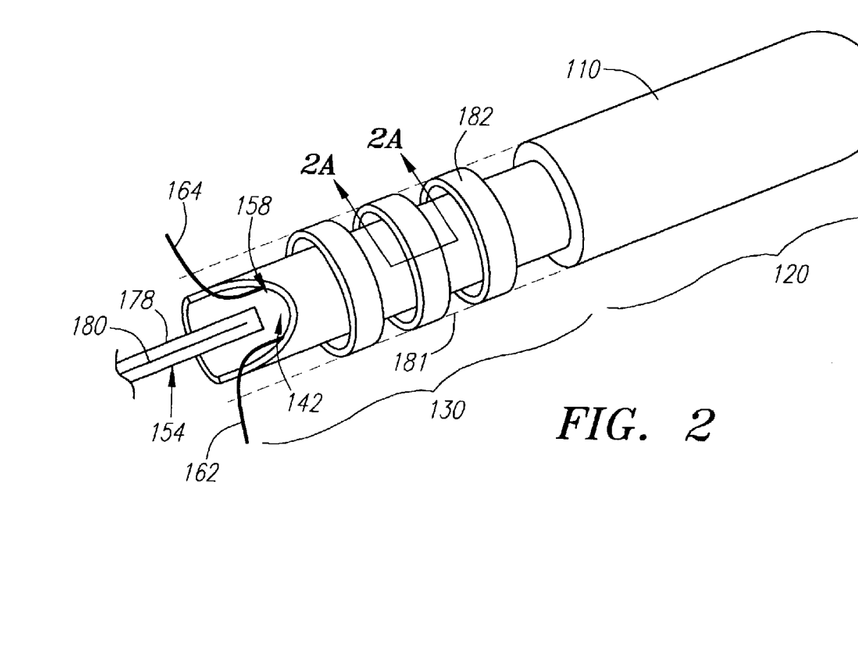
FIG. 2 is a perspective view of the distal catheter assembly of FIG. 1.

Referring to FIGS. 1 and 2, a single-member front-loaded distal catheter assembly 100 comprises a hollow ablation electrode 110 that includes a cap-shaped head section 120, a cylindrical neck section 130, and a main cavity 140 formed therein. The head section 120 of the electrode 110 forms a rounded semi-enclosed distal tip 170 that includes a narrow open channel 172 that distally leads to a distal opening 174 and proximally leads to the cavity 140. The neck section 130 of the electrode 110 forms an open proximal mounting member 150 having a proximal opening 142. In the illustrated embodiment, the ablation electrode 110 forms a single member unibody design that is composed of a suitably biocompatible, yet electrically conductive material, such as a 90/10 platinum iridium alloy.

As illustrated best in FIG. 1, the assembly 100 further comprises a thermally and magnetically sensitive sensor 160 and a thermistor 176, which are located in the main cavity 140 and channel 172, respectively. The sensor 160 and thermistor 176 can be suitably affixed within the cavity 140 and channel 172 by, e.g., using a potting material 152, such as an epoxy or UV adhesive. The sensor 160 and thermistor 176 comprise sensor wires 162 and thermistor wires 164 that extend proximally therefrom.

The assembly 100 further includes a steering assembly 154 and RF wire 156 that are attached, and preferably soldered, to the inside surface of the proximal member 150. Potting material 152 is applied to the steering assembly 154 and RF wire 156 to maintain the structural integrity of the catheter assembly 100. The steering assembly 154 comprises a resilient center support 178 on which two steering wires 180 are soldered or spot-welded. The center support 178 is composed of a flat resilient material, such as stainless steel. The distal end of the center support 178 is mounted to the proximal mounting member 150, and the distal ends of the steering wires 180 are suitably mounted on opposite surfaces of the center support 178 using a heat generating means, e.g., by soldering. The proximal ends of these steering wires 180 are connected to a suitable proximal steering assembly (not shown), the operation of which provides tension to one of the wires 180, thereby bending the assembly 100 in a predetermined direction to provide steering capability thereto.

Figure 2A:
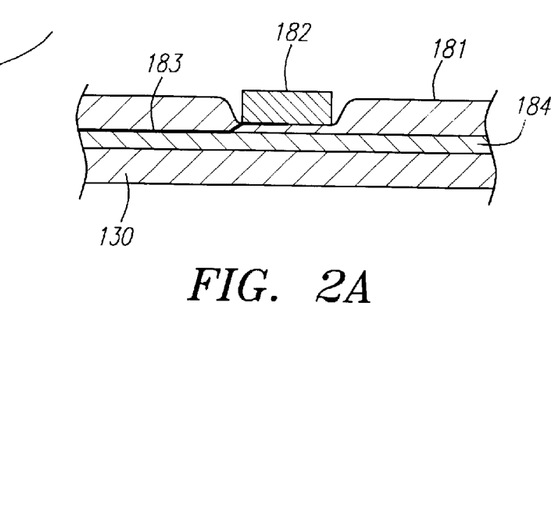
FIG. 2A is a cross-sectional view of the distal catheter assembly of FIG. 1 taken along the line 2A—2A of FIG. 2.

Referring specifically to FIGS. 2 and 2A, the assembly 100 comprises a catheter tube 181, the distal end of which (shown in phantom) is disposed over the neck section 130 of the electrode 110. The assembly 100 further comprises a multitude of mapping ring electrodes 182, which are suitable mounted around the catheter tube 181 adjacent the neck section 130 of the electrode 110, e.g., by interference fit. Signal wires 183 are suitably mounted to the underside of the mapping ring electrodes 182 and extend through an opening (not shown) in the catheter tube 181 and proximally out through a catheter lumen (also not shown). To electrically isolate the signal wires 183 from the ablation electrode 110, a thin dielectric layer 184, such as polyimide, is disposed between the inner surface of the catheter tube 181 and the outer surface of the neck section 130.

To provide a mounting or soldering area that is located away from the sensor 160, the length of the proximal member 150 is sized to extend proximally from the sensor 160. In this manner, a substantial amount of heat created by the soldering iron is dissipated before it is conducted to the sensor 160. Also, the length of the proximal member 150 allows the steering assembly 154 and RF wire 156, which typically comprise components that are made of a ferromagnetic material, such as stainless steel, to be located away from the sensor 160 so as not to magnetically affect it.

As can be seen in FIGS. 1 and 2, the assembly 100 comprises a window, and specifically a cutout 158, formed in the neck section 130 of the electrode 110. This provides a multitude of advantages to the manufacturing process. For example, the cutout 158 provides the assembler with a better view of the solder location, which would otherwise be difficult, if not impossible, to view. Also, the cutout 158 provides more space to locate the soldering iron on the solder area, which would otherwise be difficult to do, given the limited space within the neck section 130 of the electrode 110. In addition, the cutout 158 provides the assembler with space to move the sensor and thermistor leads 162 and 164 away from the solder area, allowing more space during the soldering process.

Figure 3:
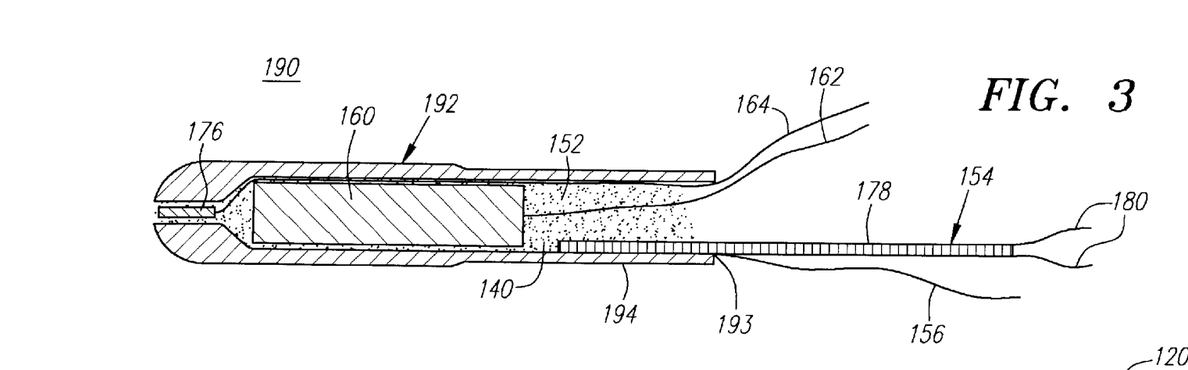
FIG. 3 is a longitudinal-sectional view of another exemplary distal catheter assembly constructed in accordance with the present inventions, wherein the distal catheter assembly is formed of a unibody ablation electrode with a front-loaded sensor, and a steering assembly is mounted thereto using non-heat generating means.
Figures 3A, 4A:
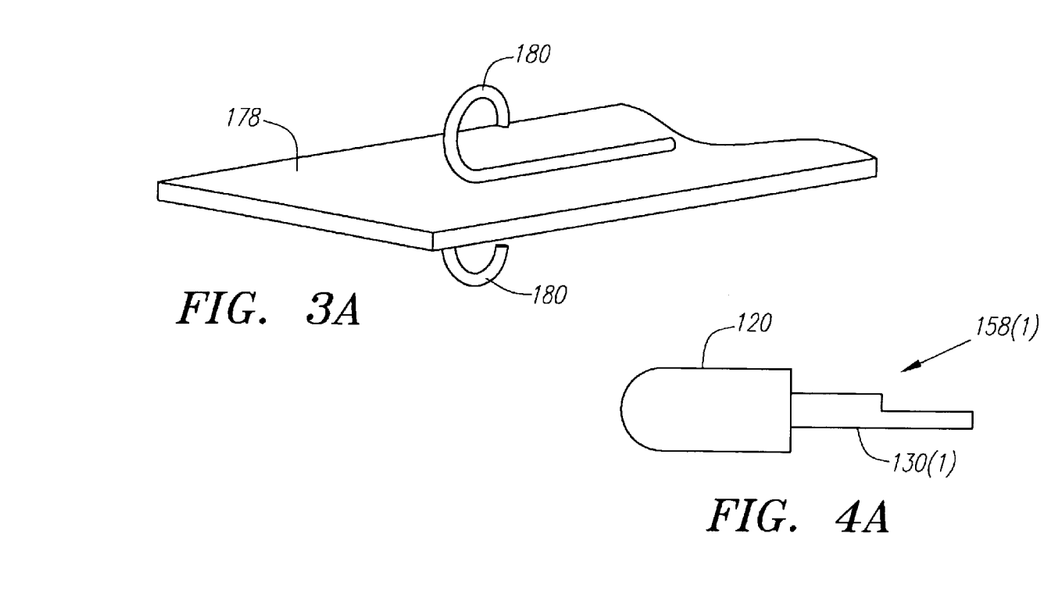
FIG. 3A is a partial perspective view of a steering assembly employed by the distal catheter assembly of FIG. 3.
FIG. 4A is a side view of an ablation electrode employed by the distal catheter assembly of FIG. 1, wherein a preferred cutout is particularly shown.
Figure 4B:
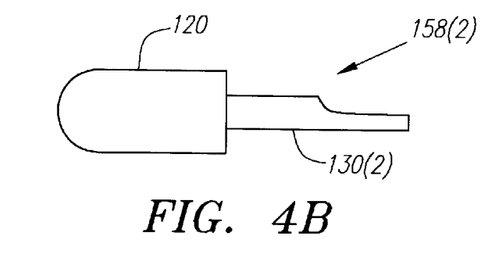
FIG. 4B is a side view of an ablation electrode employed by the distal catheter assembly of FIG. 1, wherein an alternatively preferred cutout is particularly shown.
Figure 4C:
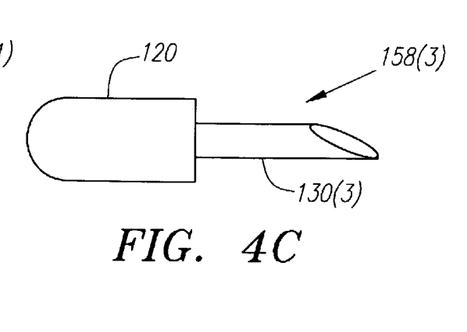
FIG. 4C is a side view of an ablation electrode employed by the distal catheter assembly of FIG. 1, wherein still another alternatively preferred cutout is particularly shown.

Referring to FIGS. 4A–4C, various types of cutouts 158 can be formed in the neck section 130 for improved ease of mounting the steering assembly 154 and RF wire 156 on the assembly 100. Specifically, a neck section 130(1) illustrated in FIG. 4A comprises a 90-degree stepped cutout 158(1). The height of the neck section 130(1) adjacent to the cutout 158(1) can be any value, giving due consideration to the relationship between the height and the structural rigidity of the neck section 130(1), i.e., as the height decreases, the structural rigidity of the neck section 130(1) decreases. The neck section 130(2) illustrated in FIG. 4B comprises an arcuate cutout 158(2). The geometry of the arcuate cutout 158(2) should be selected to maintain the structural rigidity of the neck section 130(2). The neck section 130(3) illustrated in FIG. 4C comprises a tapered cutout 158(3). In each of the neck sections 130 illustrated in FIGS. 4A–4C, the cutouts 158 are formed to expose an inner surface of the neck section 130 to facilitate the manufacturing process. It should be noted that cutouts that do not have sharp corners, such as the cutouts 158(2) and 158(3) illustrated in FIGS. 4B and 4C are more preferable than cutouts that do have sharp corners, such as the cutout 158(1) illustrated in FIG. 4A, since sharp corners typically cause stress points that are more prone to fracture when subjected to stress.

Having now described the structure of the catheter assembly 100, we now describe a method of assembling it. First, the sensor 160 and thermistor 176 are potted within the respective cavity 140 and a channel 172 of the ablation electrode 110 using the potting material 152. The thermistor 176 is located within the channel 172 by front-loading it through the proximal opening 172 of the neck section 130, and then the sensor 160 is located within the cavity 140 by front-loading it through the proximal opening 142 of the neck section 130. Alternatively, the thermistor 176 can be located within the channel 172 by back-loading it through the distal opening 174 of the head section 120 prior or subsequent to the loading of the sensor 160.

Once the sensor 160 and thermistor 176 are installed within the electrode 110, a heat sink fixture 800 (shown in FIGS. 5A–5D) can be used to provide a stable hold on the assembly 100, as well as to facilitate the dissipation of heat during the soldering process. The use of the heat sink fixture 800 is especially important in assembling the assembly 100, because the soldering of RF wires 156 and steering assembly 154 generally occurs after the sensor 160 has already been incorporated into the assembly 100. Thus, to protect the sensor 160 from heat damage, the assembly 100 should preferably be placed in the fixture 800 prior to any soldering operations.

Figures 5A, 5B:
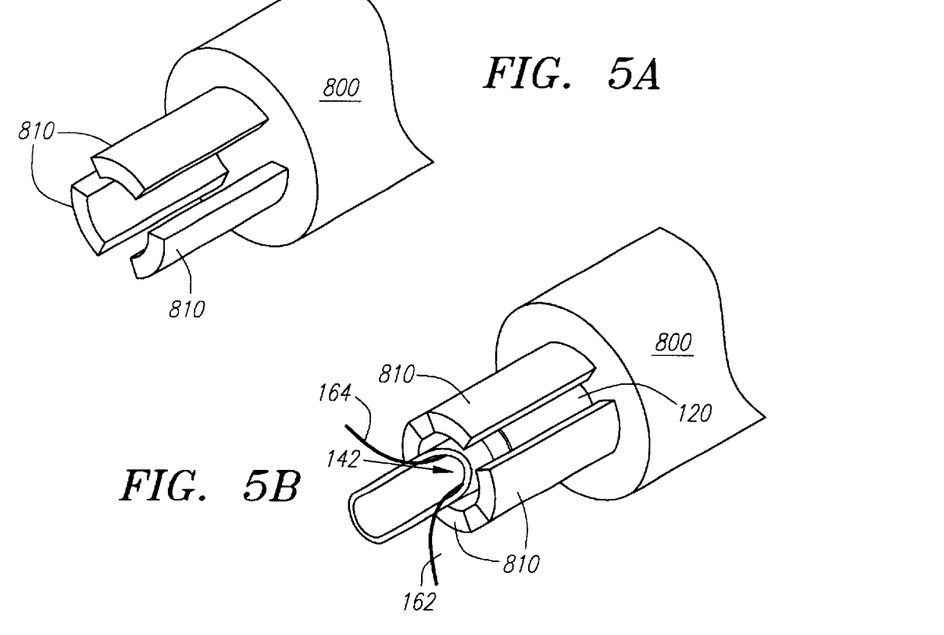
FIG. 5A is a perspective view of an open heat sink fixture used to hold the distal catheter assembly of FIG. 1.
FIG. 5B is a perspective view of the heat sink fixture of FIG. 5A, wherein an ablation electrode is particularly shown mounted therein.
Figures 5C, 5D:
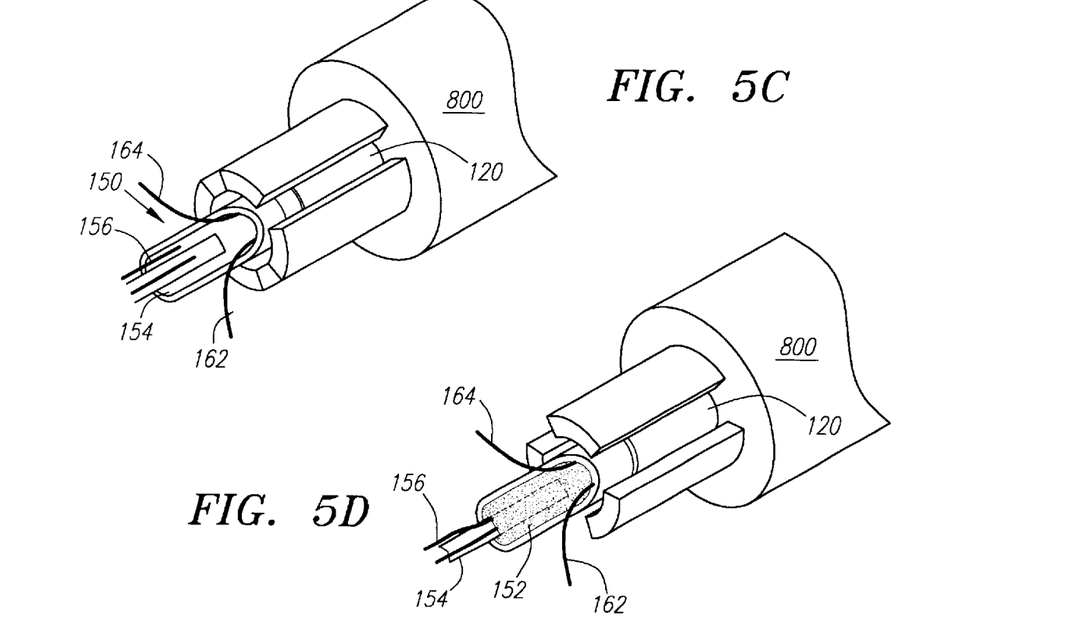
FIG. 5C is a perspective view of the heat sink fixture of FIG. 5B, wherein a sensor is particularly shown mounted within the ablation electrode.
FIG. 5D is a perspective view of the heat sink fixture of FIG. 5C, wherein a sensor is particularly shown potted within the ablation electrode.

As illustrated in FIG. 5A, the fixture 800 includes three sleeve arms 810, which are composed of a thermally conductive material, for example, a beryllium copper alloy. The fixture 800 can be operated to close the sleeve arms 810, e.g., by pneumatic means. To this end, the head section 120 of the electrode 110 is temporarily mounted within the arms 810 of the heat sink fixture 800, and the sensor and thermistor wires 162 and 164 are then carefully pulled out through the proximal opening 142 (FIG. 5B). The RF wire 156 and steering assembly 154 are then soldered to the inside surface of the proximal mounting member 150 (FIG. 5C). As previously described above, the positional relationship between the proximal mounting member 150 and the sensor 160 is such that the thermal energy generated by the soldering process and any magnetic field produced by the steering assembly 154 and RF wire 156 substantially dissipates before it reaches the sensor 160. The heat sink fixture 800 further facilitates the dissipation of heat away from the head section 120 of the electrode 110, and thus away from the sensor 160.

Next, the portion of the cavity 140 proximal to the sensor 160 is potted with the potting material 152 to maintain the structural integrity of the assembly 100 (FIG. 5D). Lastly, the dielectric layer 184 is disposed around the outer surface of the neck section 130, and the catheter tube 181 and ring electrodes 182 are interference fit around the dielectric layer 184, providing a secure and electrically isolated mount to the ablation electrode 110.

Referring to FIG. 3, a single-member front-loaded distal catheter assembly 190 is similar to the afore-described catheter assembly 100, with the exception that the steering assembly 154 is not mounted to the proximal member using heat generating means, but rather is mounted thereto using non-heat generating means.

Specifically, the catheter assembly 190 comprises an ablation electrode 192 that includes a proximal member 194 to which the steering assembly 154 and RF wire 156 are mounted. The RF wire 156 is soldered to the inside or outside of an edge 193 of the proximal member 194. As will be described below, this and the low profile of the RF wire allows enough space for the sensor 160 to be front-loaded into the main cavity 140. Like with the catheter assembly 100, the distal ends of the steering wires 180 are suitably mounted on opposite surfaces of the center support 178, e.g., by soldering or spot-welding, to form the steering assembly 154. Unlike with the catheter assembly 100, however, the steering assembly 154 is not soldered to, but is merely potted within the proximal mounting member 194 using potting material 152.

To improve the adhesion of the steering assembly 154 to the proximal mounting member 194, the inside surface of the proximal mounting member 194 is preferably roughened prior to potting the steering assembly 154 thereto. Additionally, as can be seen in FIG. 3A, the distal ends of the steering wires 180 are curled or kinked away in a plane perpendicular to the surface of the center support 178 to provide a more reliable mechanical hold between the steering assembly 154 and the potting material 152. Alternatively, the steering wires 180 may be curled or kinked in a plane parallel to the surface of the center support 178. As can be seen in FIG. 3, the proximal member 194 does not include a cutout, since the RF wire is soldered to the edge 193 of the proximal member 194, and minimal space is required to pot the steering assembly 154 within the proximal member 194.

The method of assembling the catheter assembly 190 is similar to that of the catheter assembly 100 with the exception that the RF wire 156 is soldered to the proximal member 194 prior to front-loading the sensor 160 and thermistor 176 into the main cavity 140, and the steering assembly 154 is mounted to the proximal member 194 using non-heat generating means. Thus, the heat sink fixture 800, although still preferably used for convenience of manufacture, need not be used to dissipate the heat away from the sensor 160.

Figure 6:
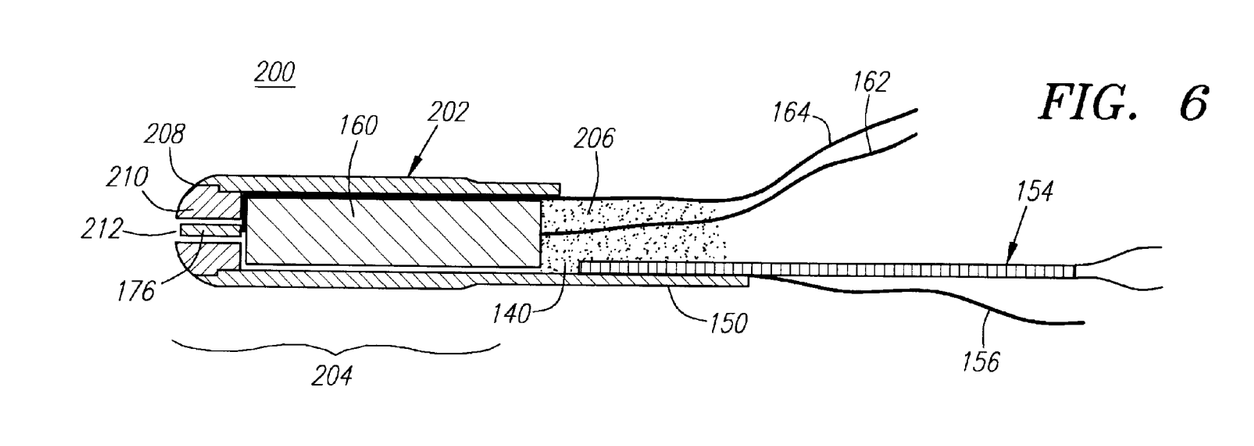
FIG. 6 is a longitudinal-sectional view of another exemplary distal catheter assembly constructed in accordance with the present inventions, wherein the distal catheter assembly is formed of a unibody ablation electrode with a back-loaded sensor.

Referring to FIG. 6, a back-loaded distal catheter assembly 200 is illustrated. The assembly 200 is similar to the afore-described assembly 100, with the exception that it includes an electrode 202 that provides for back-loading of the sensor 160 therein. To this end, a head section 204 of the electrode 202 includes a distal opening 208 that is large enough to allow the sensor 160 to be inserted within a main cavity 206 formed within the electrode 202. The assembly 200 further includes a plug 210 that is snugly fit within the distal opening 208, e.g., in a threaded arrangement. The plug 210 has a narrow channel 212, which houses the thermistor 176. Alternatively, use of the plug 210 can be foregone if the sensor 160 and corresponding distal opening 208 are small enough.

The method of assembling the assembly 200 is generally the same as the method of assembling the assembly 100, with the exception that the sensor 160 is back-loaded into the main cavity 140 of the electrode 202 after the steering assembly 154 and RF wire 156 are soldered to the proximal mounting member 150. After the sensor 160 is mounted within the main cavity 140, the plug 210 is installed within the distal opening 208 to partially seal the main cavity 140. Thus, this back-loading procedure eliminates the risk of exposure of the sensor 160 to heat generated by the soldering process. Further, under this approach, the use of the previously described heat sink fixture 800, although preferably used for ease of manufacture, may be foregone, since heat generated by the soldering process dissipates prior to mounting the sensor 140.

Figure 7:
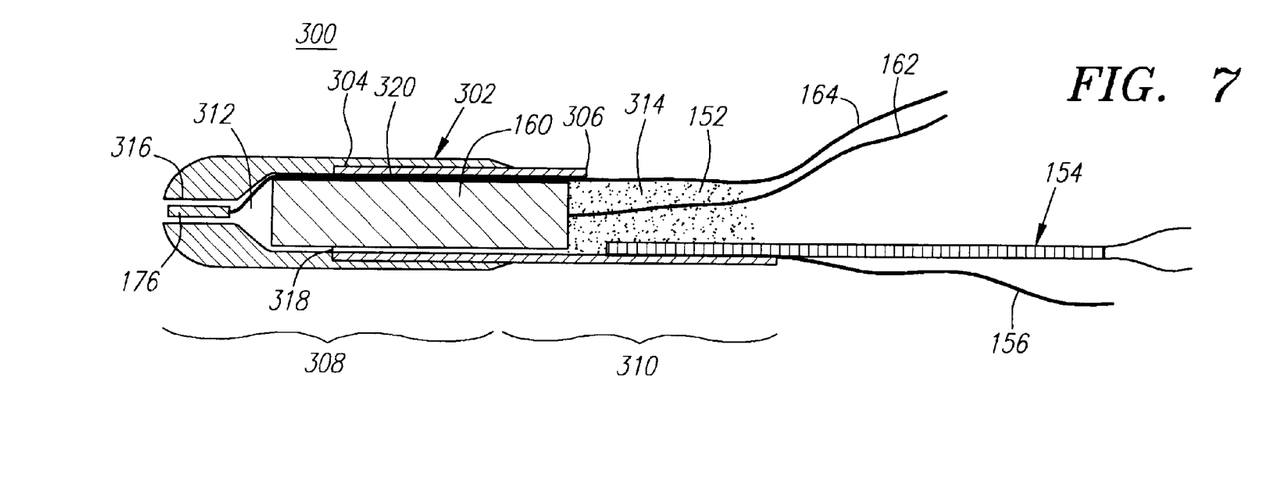
FIG. 7 is a longitudinal-sectional view of still another exemplary distal catheter assembly constructed in accordance with the present inventions, wherein the distal catheter assembly is formed of a preferred two-piece ablation electrode.

Referring to FIG. 7, a two-piece distal catheter assembly 300 is illustrated. The assembly 300 is similar to the afore-described assembly 100, with the exception that it comprises an ablation electrode 302 formed by two separate axially aligned distal and proximal members 304 and 306, respectively. In particular, the distal member 304 forms a cap-shaped head 308, and the proximal member 306 forms a cylindrically-shaped neck 310. The distal member 304 includes a distal cavity 312, and the proximal member 306 includes a proximal cavity 314, which together form a main cavity 320 when the distal and proximal members 304 and 306 are mated together, e.g., in a threaded arrangement or bonded together using silver epoxy. The distal member 304 further comprises a distal channel 316, and the proximal member 306 comprises a distal opening 318. The sensor 160 is mounted within the main cavity 320, and the thermistor 176 is disposed in the distal channel 316. As illustrated, the distal and proximal members 304 and 306 can be characterized as respective female and male members, with the distal end of the proximal member 306 fitting snugly within the proximal end of the distal member 304. As will be described in further detail below, this arrangement allows the sensor 160 and thermistor 176 to be fully mounted within the ablation electrode 302, well after the soldering process takes place.

Figure 8:
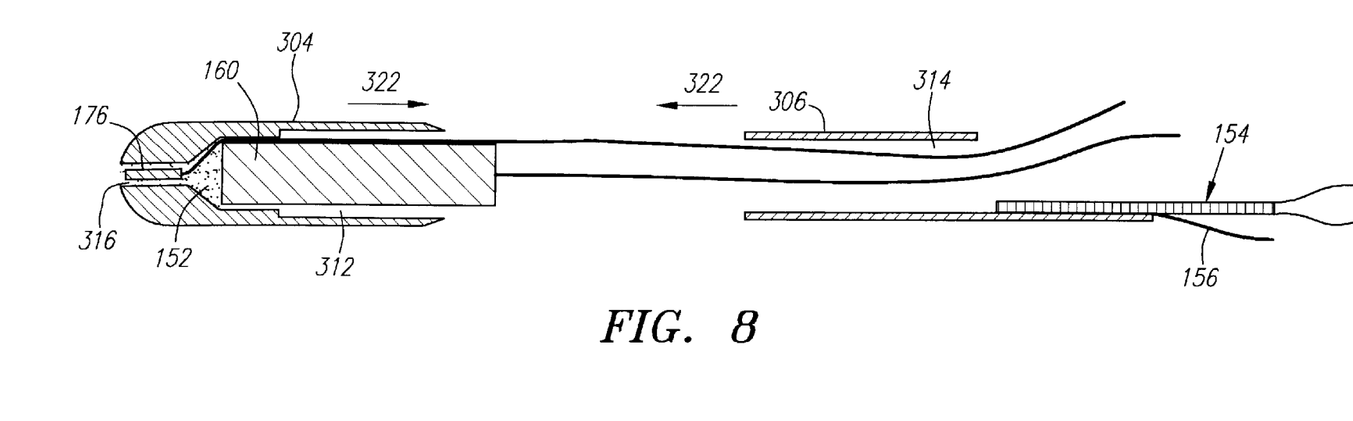
FIG. 8 is an exploded side view of the distal catheter assembly of FIG. 7, wherein a sensor is being front-loaded into the distal member.
Figure 9:
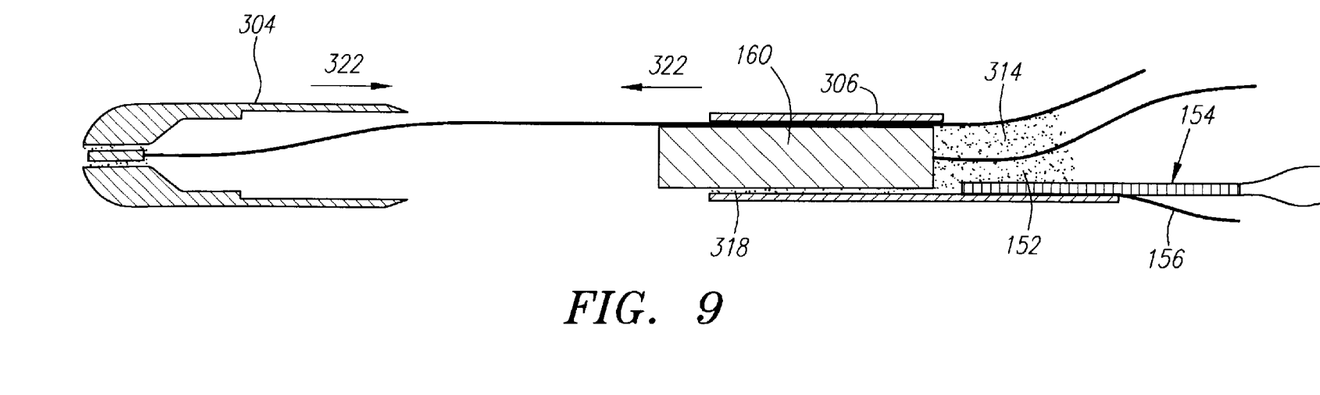
FIG. 9 is an exploded side view of the distal catheter assembly of FIG. 7, wherein a sensor is being back-loaded into the proximal member.

The method of assembling the assembly 300 is generally the same as the method of assembling the assembly 100, with the exception that the internal components of the assembly 300, for example the sensor 160, the thermistor 176, the steering assembly 154 and the RF wire 156 are mounted when the distal and proximal members 304 are 306 are still separate. For example, the sensor 160 and thermistor 176 can be respectively mounted within the distal cavity 312 and the distal channel 316 of the distal member 304, using potting material 152, and the steering assembly 154 and RF wire 156 can be soldered within the proximal cavity 314 of the proximal member 306 when the distal and proximal members 304 and 306 are separate, as illustrated in FIG. 8. Alternatively, the steering assembly 154 and RF wire 156 can be soldered within the proximal cavity 314 of the proximal member 306, and then the sensor 160 can be back-loaded into the same proximal cavity 314 via the distal opening 318, as illustrated in FIG. 9. The steering assembly 154, RF wire 156, and sensor 160 are then potted with the potting material 152.

In any event, after mounting the internal components, i.e., the sensor 160, thermistor 176, steering assembly 154, and RF wire 156, the proximal and distal members 304 and 306 are then fitted together (in a direction indicated by arrows 322) to form the integral ablation electrode 302 and main cavity 320. Then the entire main cavity 320 is potted with the potting material 152. Thus, the sensor 160 does not come into contact with the proximal member 306 until well after the soldering process has taken place, thereby eliminating the risk that heat generated by the soldering process is transferred to the sensor 160. This method also allows cleaning of the solder area, and prevents the sensor and thermistor wires 162 and 164 from hindering the soldering process.

Figure 10:
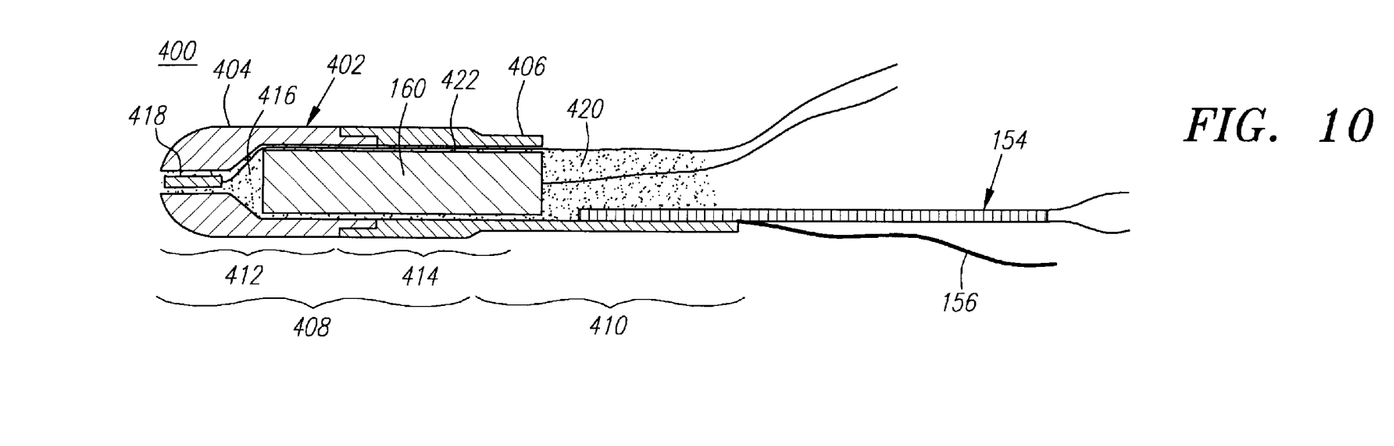
FIG. 10 is a longitudinal-sectional view of still another exemplary distal catheter assembly constructed in accordance with the present inventions, wherein the distal catheter assembly is formed of an alternatively preferred two-member ablation electrode.

Referring to FIG. 10, another two-piece distal catheter assembly 400 is illustrated. The assembly 400 differs from the afore-described assembly 300 in that the head of the ablation electrode is formed of two pieces. In particular, the assembly 400 comprises an ablation electrode 402 that includes a distal member 404 that forms only the distal end 412 of a cap-shaped head 408, and a proximal member 406 that forms the proximal end 414 of the head 408 and the entirety of a cylindrically-shaped neck 410. Like the assembly 300, the distal member 404 includes a distal cavity 416 and distal channel 418, and the proximal member 406 includes a proximal cavity 420, which together form a main cavity 422 when the distal and proximal members 404 and 406 are mated together, e.g., in a threaded arrangement or bonded together using silver epoxy.

As illustrated, the distal and proximal members 404 and 406 can be characterized as respective male and female members, with the proximal end of the distal member 404 fitting snugly within the distal end of the proximal member 406. Like the assembly 300, this arrangement allows the sensor 160 to be fully mounted within the ablation electrode 402 well after the soldering process takes place. The method of assembling the assembly 400 is similar to the method of assembling the assembly 300 in that, prior to affixing the distal and proximal members 404 and 406 together, the steering assembly 154 and RF wire 156 are mounted within the proximal cavity 420 of the proximal member 406 and the sensor 160 is either mounted within the distal cavity 416 of the distal member 404 (similarly to the assembly 300 shown in FIG. 8), or back-loaded into the proximal cavity 420 of the proximal member 406 (similar to the assembly 300 shown in FIG. 9). In any event, the advantages described with respect to the assembly 300 are achieved.

Figure 11:
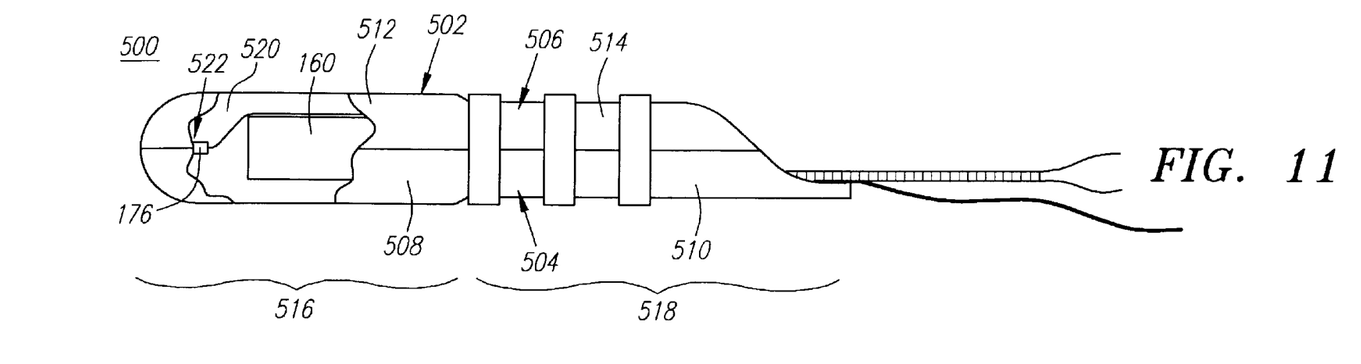
FIG. 11 is a longitudinal-sectional view of still another exemplary distal catheter assembly constructed in accordance with the present inventions, wherein the distal catheter assembly is formed of a preferred clamshell ablation electrode.

Referring to FIG. 11, a clamshell distal catheter assembly 500 is illustrated. The assembly 500 is similar to the afore-described assembly 100, with the exception that it is formed of two clamshell members. In particular, the assembly 500 comprises an ablation electrode 502 formed by complementary bottom and top lateral housing sections 504 and 506, respectively, which for purposes of this specification, are housing sections whose lateral sides fit together in a complementary fashion to form a composite housing. It should be noted that the terms "top" and "bottom" are used for purposes of illustration, and it should be understood that the use of such terms when identifying certain features on an actual distal catheter assembly will change with the particular orientation of the distal catheter assembly.

The bottom housing section 504 comprises a bottom head section 508 and bottom neck section 510, and the top housing section 506 comprises a top head section 512 and top neck section 514, which when affixed to each other using an electrically conductive bonding material, such as silver epoxy, forms a cap-shaped head 516 and cylindrically-shaped neck 518 having a main cavity 520 and distal channel 522 formed therein. As can be seen, the sensor 160 and thermistor 176 are respectively mounted within the main cavity 520 and distal channel 522. Alignment of the housing sections 504 and 506 is accomplished by a pin and hole arrangement. Specifically, the bottom housing section 504 includes a pair of pinholes 524, and the top housing section 506 includes a pair of complementary pins 526 that fit together to align the respective housing sections 504 and 506 (shown in FIG. 12). As will be described in further detail below, this arrangement allows the sensor 160 and thermistor 176 to be fully mounted within the ablation electrode 502, well after the soldering process takes place. Alternatively, as illustrated in FIG. 12A, either the bottom housing section 504 can have one or more ridges 525, and the top housing section 506 can have one or more complementary indentations 527 that engage the ridges 525 to provide alignment between the respective sections 504 and 506.

Figure 12:
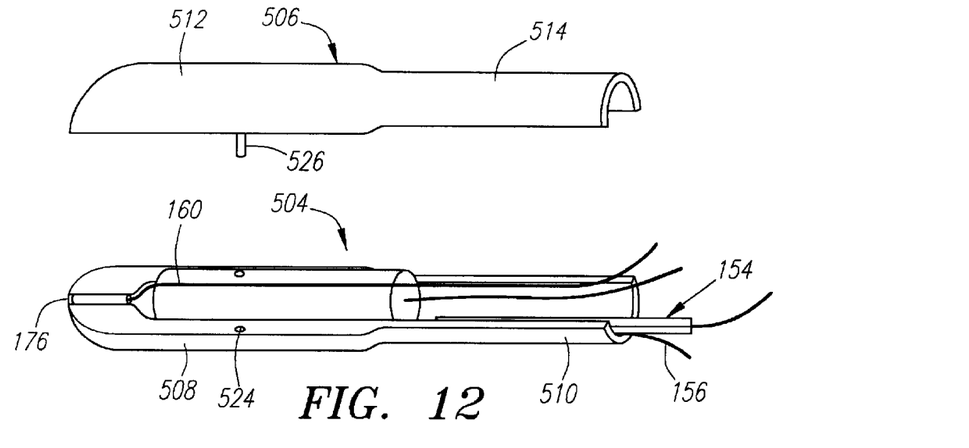
FIG. 12 is an exploded side view of the distal catheter assembly of FIG. 11, wherein a pin and hole arrangement is used to align the two members of the ablation electrode.
Figure 12A:
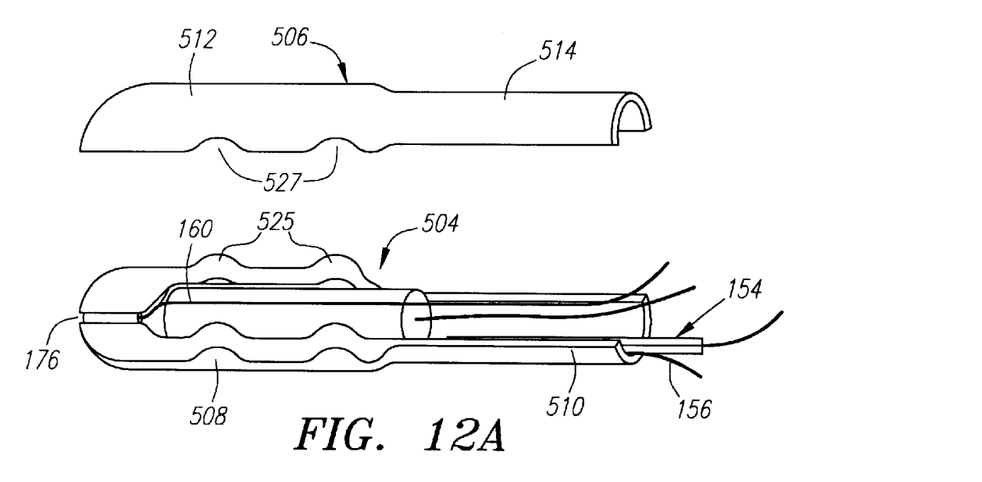
FIG. 12A is an exploded side view of the distal catheter assembly of FIG. 11, wherein a ridge and indentation arrangement is used to align the two members of the ablation electrode.

Referring to FIG. 12, the assembly 500 is assembled by first soldering the steering assembly 154 and RF wire 156 to the bottom neck section 510. After the heat generated by the soldering process has dissipated from the bottom housing section 504, the sensor 160 and thermistor 176 are then mounted within the bottom head section 508, e.g., by potting with an epoxy. Alternatively, the sensor 160 and thermistor 176 can be similarly mounted within the top head section 512. In any event, after the internal components are mounted, the housing sections 504 and 506 are affixed to each other, with the pair of complementary pinholes 524 and pins 526 being in engagement with each other for purposes of alignment.

Figure 13:
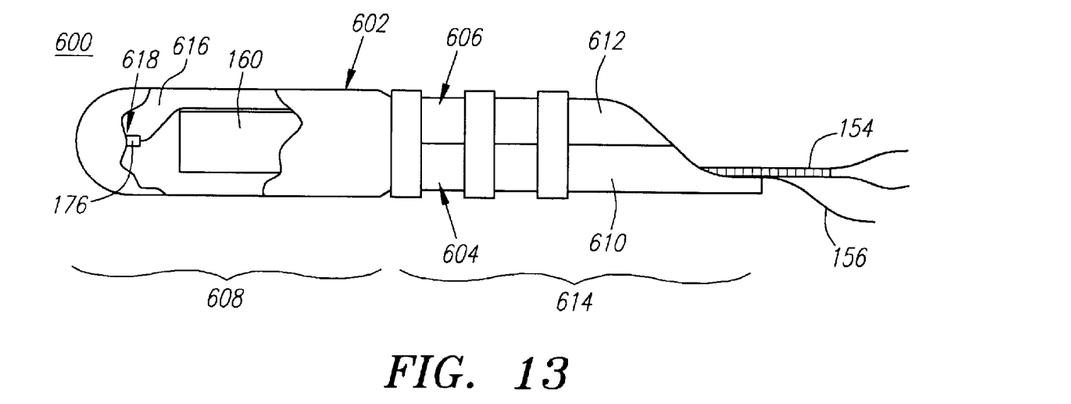
FIG. 13 is a longitudinal-sectional view of still another exemplary distal catheter assembly constructed in accordance with the present inventions, wherein the distal catheter assembly is formed of an alternatively preferred clamshell ablation electrode.

Referring to FIG. 13, another clamshell distal catheter assembly 600 is illustrated. The assembly 600 is similar to the afore-described assembly 500, with the exception that only the neck is formed of two clamshell members. In particular, the assembly 600 comprises an ablation electrode 602 formed by bottom and top complementary lateral housing sections 604 and 606, respectively. The bottom housing section 604 comprises a cap-shaped head 608 and a bottom neck section 610, and the top housing section 606 only comprises a top neck section 612. When the housing sections 604 and 606 are affixed to each other using an electrically conductive bonding material, such as silver epoxy, a cylindrically-shaped neck 614, along with the head 608, is formed, with the sensor 160 and the thermistor 176 being respectively mounted within a main cavity 616 and distal channel 618. To facilitate the mounting of the sensor 160 and thermistor 176, a proximal opening 620 and distal opening (not shown) are provided in the head 608. Again, alignment of the housing sections 604 and 606 is accomplished by a pin and hole or ridge and indentation arrangement.

Figure 14:
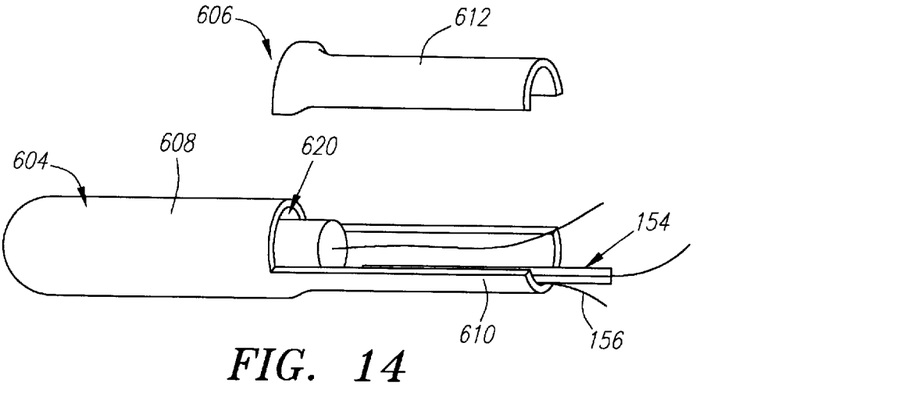
FIG. 14 is an exploded side view of the distal catheter assembly of FIG. 13.

Referring to FIG. 14, the assembly 600 is assembled by first soldering the steering assembly 154 and RF wire 156 to the bottom neck section 610. Alternatively, the steering assembly 154 and RF wire 156 can be similarly mounted within the top neck section 612. After the heat generated by the soldering process has dissipated from the bottom housing section 604, the sensor 160 and thermistor 176 are then mounted within the head 608, e.g., by potting with an epoxy. In the illustrated embodiment, the sensor 160 is front-loaded into the head 608 through the proximal opening 620, and the thermistor 176 is back-loaded into the head 608 through the distal opening (not shown). The absence of the top housing section 606 allows suitable clearance for front-loading of the sensor 160 through the proximal opening 620. After the internal components are mounted, the bottom and top housing sections 604 and 606 are affixed to each other.

Figure 15:
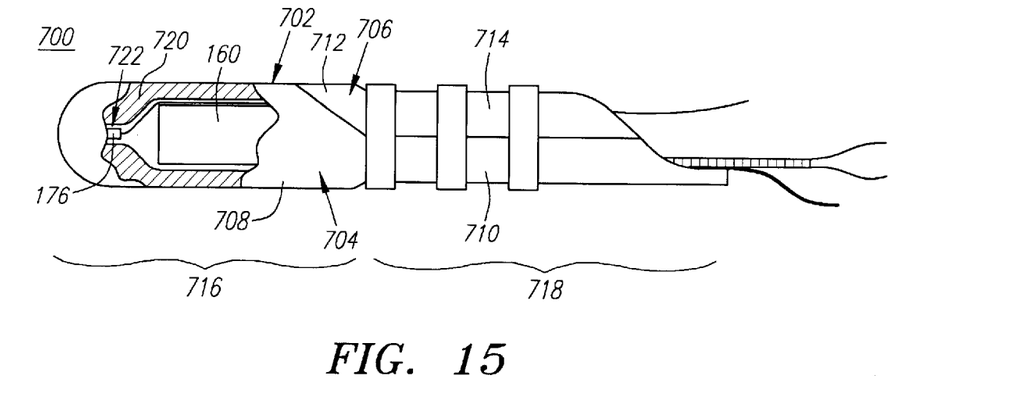
FIG. 15 is a longitudinal-sectional view of still another exemplary distal catheter assembly constructed in accordance with the present inventions, wherein the distal catheter assembly is formed of another alternatively preferred clamshell ablation electrode.

Referring to FIG. 15, still another clamshell distal catheter assembly 700 is illustrated. The assembly 700 is similar to the afore-described assembly 500, with the exception that the neck and only a portion of the head is formed of two clamshell members. In particular, the assembly 700 comprises an ablation electrode 702 formed by bottom and top complementary lateral housing sections 704 and 706, respectively. The bottom housing section 704 comprises a bottom head section 708 and a bottom neck section 710, and the top housing section 706 also comprises a top head section 712 and a top neck section 714. When the housing sections 704 and 706 are affixed to each other using an electrically conductive bonding material, such as silver epoxy, a cap-shaped head 716 and cylindrically-shaped neck 718 are formed, with the sensor 160 and thermistor 176 being respectively mounted within a main cavity 720 and distal channel 722. As can be seen, only the proximal end of the head 716 is formed by mounting of the housing sections 704 and 706. To facilitate the mounting of the sensor 160 and thermistor 176, a proximal opening 724 (illustrated in FIG. 16) and distal opening (not shown) are provided in the head 716. Again, alignment of the housing sections 704 and 706 is accomplished by a pin and hole arrangement or a ridge and indentation arrangement.

Figure 16:
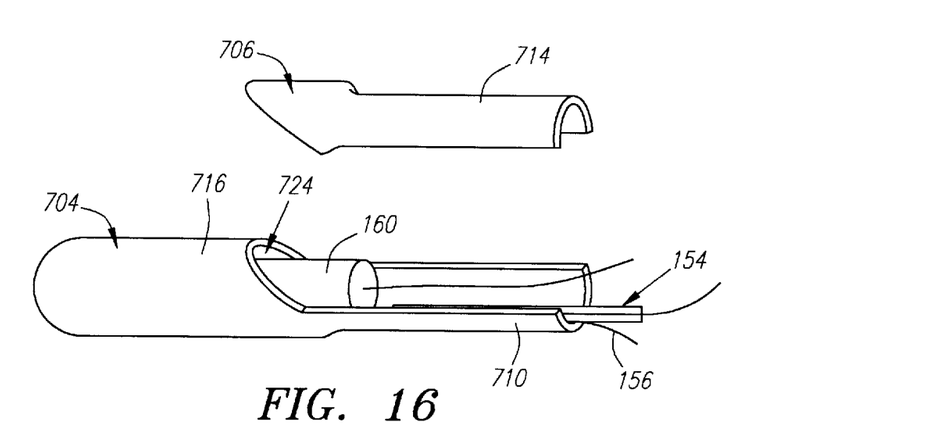
FIG. 16 is an exploded side view of the distal catheter assembly of FIG. 15.

Referring to FIG. 16, the assembly 700 is assembled by first soldering the steering assembly 154 and RF wire 156 to the bottom neck section 710. Alternatively, the steering assembly 154 and RF wire 156 can be similarly mounted within the top neck section 714. After the heat generated by the soldering process has dissipated from the bottom housing section 704, the sensor 160 and thermistor 176 are then mounted within the bottom head section 708, e.g., by potting with an epoxy. In the illustrated embodiment, the sensor 160 is front-loaded into the bottom head section 708 through the proximal opening 724, and the thermistor 176 is back-loaded into the bottom head section 708 through the distal opening (not shown). The absence of the top housing section 706 allows suitable clearance for front-loading of the sensor 160 through the proximal opening 724. After the internal components are mounted, the housing sections 704 and 706 are affixed to each other.

Although particular embodiments of the present invention have been shown and described, it will be understood that it is not intended to limit the invention to the preferred embodiments and it will be obvious to those skilled in the art that various changes and modifications may be made without departing from the spirit and scope of the present invention. Thus, the invention is intended to cover alternatives, modifications, and equivalents, which may be included within the spirit and scope of the invention as defined by the claims.

All publications, patents, and patent applications cited herein are hereby incorporated by reference in their entirety for all purposes.

What is claimed is:

1. A method for assembling a distal catheter assembly, comprising:

mounting a first catheter component within a first lateral housing section, said first component being adversely affected in the presence of an environmental condition;

mounting a second catheter component within a complementary second lateral housing section, said mounting of said second component creating said environmental condition; and affixing said second housing section to said first housing section subsequent to mounting said first and second components whereby a composite housing is formed for said first and second components.

2. The method of claim 1, wherein said composite housing comprises an ablation electrode.

3. The method of claim 1, further comprising mounting a thermistor within said first housing section.

4. The method of claim 1, wherein said first housing section comprises one or more pins, and said second housing section comprises one or more holes, wherein said first housing section is affixed to said second housing section by disposing said one or more pins within said one or more holes.

5. The method of claim 1, wherein said environmental condition is thermal energy.

6. The method of claim 1, wherein said environmental condition is magnetical energy.

7. The method of claim 1, wherein said first component comprises a magnetic sensor.

8. The method of claim 1, wherein said second component comprises a steering assembly.

9. The method of claim 1, wherein said second component comprises an RF lead.

10. The method of claim 1, further comprising isolating said first component from said environmental condition.

11. A method of assembling a distal catheter assembly, comprising:

mounting a second catheter component within a first lateral housing section, said mounting of said second component creating an environmental condition;

mounting a first catheter component within said first lateral housing section subsequent to said mounting of said second catheter component, said first component being adversely affected in the presence of said environmental condition; and affixing a second complementary lateral housing section to said first housing section subsequent to said mounting of said first and second components to form a composite housing.

12. The method of claim 11, wherein said composite housing comprises an ablation electrode.

13. The method of claim 11, further comprising mounting a thermistor within said first housing section.

14. The method of claim 11, wherein said first housing section comprises one or more pins, and said second housing section comprises one or more holes, wherein said first housing section is affixed to said second housing section by disposing said one or more pins within said one or more holes.

15. The method of claim 11, wherein said environmental condition is thermal energy.

16. The method of claim 11, wherein said environmental condition is magnetic energy.

17. The method of claim 11, wherein said first component comprises a magnetic sensor.

18. The method of claim 11, wherein said second component is mounted proximal to said first component.

19. The method of claim 11, wherein said second component comprises a steering assembly.

20. The method of claim 11, wherein said second component comprises an RF lead.

21. The method of claim 11, wherein said second component is mounted within said first housing section by means of heat generation.

22. The method of claim 11, wherein said second component is soldered within said first housing section.

23. The method of claim 11, further comprising isolating said first component from said environmental condition.

* * * * *